United States Patent [19]

Manziek

[11] 4,355,140

[45] Oct. 19, 1982

[54] BORANE REDUCING RESINS

[75] Inventor: Larry Manziek, Lansdale, Pa.

[73] Assignee: Rohm and Haas Company, Philadelphia, Pa.

[21] Appl. No.: 226,656

[22] Filed: Jan. 21, 1981

Related U.S. Application Data

[63] Continuation-in-part of Ser. No. 749,560, Dec. 10, 1976, abandoned.

[51] Int. Cl.$^3$ .............................................. C08F 8/42
[52] U.S. Cl. ................................. 525/329.4; 525/337; 525/338; 528/481; 525/326.1
[58] Field of Search ............... 525/337, 332, 329, 336, 525/338

[56] References Cited

U.S. PATENT DOCUMENTS

| | | | |
|---|---|---|---|
| 2,731,454 | 1/1956 | Edmonds | 525/337 |
| 3,520,865 | 7/1970 | Pumpus et al. | 525/337 |
| 3,679,646 | 7/1972 | Bristol | 525/337 |
| 4,029,706 | 6/1977 | Cosby | 525/337 |
| 4,277,576 | 7/1981 | Straub et al. | 525/337 |
| 4,281,086 | 7/1981 | Gaul et al. | 525/337 |

OTHER PUBLICATIONS

Solid Phase Phosphorous Reagents–Regen et al., Jour. Org. Chem., vol. 40, No. 11, (1975), pp. 1669–1670.

*Primary Examiner*—William F. Hamrock

[57] ABSTRACT

This invention relates to solid nonionic crosslinked resins containing amine or phosphine borane adducts capable of being used as reducing agents for metal ions, aldehydes, ketones, alkenes and the like.

4 Claims, No Drawings

BORANE REDUCING RESINS

BACKGROUND OF THE INVENTION

This is a continuation-in-part of U.S. patent application Ser. No. 749,560 filed Dec. 10, 1976, abandoned.

It is known in the art [see M. K. Hallensleben, *J. Polymer Science*: Symposium No. 47, 1–9 (1974)] that linear and crosslinked copolymers of 4-vinylpyridine borane, 4-vinylpyridine, and styrene can be prepared and used as polymeric reducing agents for aldehydes and ketones. It is also reported in the literature [see E. ernia and F. Gasparini, *J. Applied Polymer Science*, vol. 19, 917–20 (1975)] that 4-vinylpyridine borane hydride polymers rapidly decompose in aqueous solutions of strong mineral acids and can only be used as reducing agents for aldehydes and ketones at or about neutral pH.

U.S. Pat. No. 3,928,293 granted Dec. 23, 1975 discloses solid crosslinked thiohydrocarbon borane hydride polymers and their use as reducing agents for aldehydes, ketones, lactones, oxides, esters, carboxylic acids, nitriles and olefins. These borane polymers, although stabile at room temperature, can release borane ($BH_3$) under conditions of reduced pressure or heat and are disclosed as being useful as a convenient means of storing borane. U.S. Pat. No. 3,609,191 granted Sept. 28, 1971 discloses polyethylene imine borane complexes which are stabile toward hydrolysis at a pH as low as 5.0. These compositions are useful as reducing agents in chemical plating baths for nickel, copper and silver in a pH range of 5 to 8. However, these products are viscous or solid polymers which range in water solubility from completely soluble to slightly soluble depending on the ratio of $BH_3$ to amino groups in the polymer. The use of ion exchange resins to extract heavy metals from aqueous solutions via ion exchange mechanisms is also reported in the art.

SUMMARY OF THE INVENTION

This invention relates to novel nonionic crosslinked resins containing amine or phosphine borane adducts of the formula:

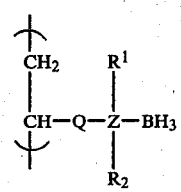   (I)

wherein
Q is a group of the formula:

$$-(CH_2)_m-T-(CH_2)_n-$$

wherein
m and n are independently integers from 0 to 3; and
T is the group

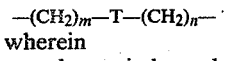

and
$R^1$ and $R^2$ are independently (a) hydrogen;
(b) ($C_1$–$C_8$) optionally substituted alkyl;
(c) ($C_6$–$C_{12}$) optionally substituted aryl; and
(d) ($C_7$–$C_{12}$) optionally substituted aralkyl; and
Z is nitrogen or phosphorus, and their use as highly selective reducing agents and as starting materials for the preparation of novel metal catalysts for use in hydrogenation reactions.

The term "alkyl" as utilized in the present specification and claims is meant to include both straight and branch chained alkyl groups which can be optionally substituted with up to three substituents, preferably with up to two substituents, more preferably with up to one substituent, selected from the group consisting of hydroxy, mercapto, fluoro, chloro, bromo, iodo, nitro, methoxy, ethoxy, isopropoxy, amino, methylamino, dimethylamino, ethylamino, diethylamino, amido, methylamido and dimethylamido.

The term "aryl" as utilized in the present specification and claims is meant to include aryl groups such as phenyl, naphthyl and biphenyl, which can be optionally substituted with up to three substituents, preferably with up to two substituents, more preferably with up to one substituent, selected from the group consisting of fluoro, chloro, bromo, iodo, nitro, methyl, ethyl, methoxy, ethoxy and trihalomethyl.

The term "aralkyl" as utilized in the present specification and claims is meant to include such aralkyl groups as benzyl, phenethyl, phenylpropyl, naphthylmethyl and naphthylethyl which can be optionally substituted with up to three substituents, preferably with up to two substituents, more preferably with up to one substituent, selected from the group consisting of fluoro, chloro, bromo, iodo, nitro, methyl, ethyl, methoxy, ethoxy and trihalomethyl.

The preferred nonionic borane resins of this invention are those wherein T is the group

Z is nitrogen; and $R^1$ and $R^2$ are independently hydrogen, ($C_1$–$C_8$) unsubstituted alkyl, ($C_6$–$C_{12}$) unsubstituted aryl or ($C_7$–$C_{12}$) unsubstituted aralkyl.

The more preferred nonionic borane resins of this invention are those where T is the group

Z is nitrogen; and $R^1$ and $R^2$ are independently hydrogen, ($C_1$–$C_4$) unsubstituted alkyl or unsubstituted phenyl, biphenyl, benzyl or phenethyl.

DETAILED DESCRIPTION OF THE INVENTION

The solid nonionic crosslinked borane reducing resins of this invention are highly selective reducing agents which are particularly useful in selectively reducing at room temperature, from both aqueous and non-aqueous media, mercury, silver, gold, platinum, palladium, rhodium, iridium, antimony, arsenic and bismuth ions; to the exclusion of copper, nickel, zinc, iron, lead, thin, cadmium, vanadium, chromium, uranium, thorium, cobalt, thallium, aluminum and the Group I and II members of the Periodic Table. These resins reduce the metal ions in solution via electron transfer and precipitate the reduced metals on and/or into the resin.

These borane resins are capable of being utilized over a wide range of pH conditions and can be utilized at pH ranges greater than about 1.0 but less than about 8.0. These resins are preferably utilized at pH ranges of from about 2.0 to about 4.0. These borane resins are not only stabile in acidic and basic media but are also air stabile as well.

The solid nonionic crosslinked borane reducing resins can also be utilized as reducing agents for aldehydes, ketones, olefins and other functional groups capable of undergoing hydroboration reactions. These reagents reduce the aldehydes, ketones, olefins and the like via hydride transfer and the resultant product can be liberated from the resin via strong acid hydrolysis. An added feature of this reduction procedure is the ability of these resins to concentrate the products onto the resin thereby effecting a concentration and a purification of the products formed before hydrolyzing them off the resin. Although the macroreticular form of the resin is preferred, the gel form or any other particulate form of the nonionic borane reducing resins of the present invention can be utilized as reducing agents.

The reduced metals which are precipitated on and/or into the nonionic borane reducing resins of the present invention can be either dissolved out of the resin via strong acid or in the case of mercury can be withdrawn by treatment with hot water. The more preferred method of obtaining the reduced precious metals from the resins is by burning the resin away from the metals since the value of the precious metals far exceeds the cost of the resin.

These nonionic borane reducing resins have an advantage over ion exchange resins in that ion exchange resins have distinct leakage problems due to the various ion exchange equilibria for each specific metal ion and ion exchanger. There is no such leakage problem due to ion exchange equilibrium kinetics in the nonionic borane reducing resins of the present invention. These resins reduce the metals to their zero oxidation state and precipitate them on and/or into the resin. Another advantage of these resins and in particular of the macroreticular resins is their ability to contain large capacities of reduced metals before breakthrough finally occurs.

A preferred embodiment of this invention is the use of the solid nonionic crosslinked amine and phosphine borane reducing resins as starting materials for the preparation of novel metal catalysts for use in hydrogenation reactions. The resultant metal containing resins can either be pyrolyzed to give a carbon-metal reduction catalyst or they can be combusted in the presence of oxygen to give the metal in a bead form. Moreover, catalysts containing known percentages of metals or of mixed metals can be formed via this process. The nonionic borane reducing resins of the present invention can be prepared by the following general synthetic routes.

In the preparation of the nonionic borane reducing resins of the present invention a suitable water-insoluble crosslinked resin having a functional group of the formula

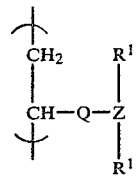
(II)

wherein Q, $R^1$, $R^2$ and Z are as defined in Formula (I) above, is reacted with a suitable protonating mineral acid such as hydrohalic, phosphoric, sulfuric and the like, preferably hydrochloric acid to form the cationic group of the formula

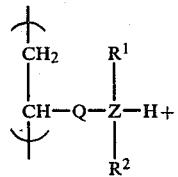
(III)

This reaction is carried out in either a batch or column process at temperatures from about 0° to about 100° C., preferably at about 20° C., in a suitable protic solvent preferably water. The amount of protonating acid used can be anywhere from 5% of the equivalents of weak base in the resin to any percentage over and above the equivalents of weak base in the resin, but is preferably utilized in a 25% excess over the equivalents of weak base in the resin. After the protonation step has taken place, the resin is then treated with a water wash to remove any excess acid and then washed thoroughly with a suitable drying solvent such as methanol, ethanol, propanol, acetone, dimethylformamide and the like or alternatively can be air or vacuum dried. In a more preferred process for this protonation step the reaction is carried out in a batch process and a stoichiometric amount of acid is added to protonate all the available protonizable groups. Longer reaction times are preferred in this process since it allows complete diffusion of the acid throughout the resin beads. The borane is preferably incorporated into the protonated resin by treating the resin either in a column or batch process with an excess of a solution of lithium, sodium or potassium borohydride dissolved in an appropriate solvent such as methanol, ethanol, dimethylformamide, monoglyme, diglyme and the like at temperatures from about 0° to about 150° C. preferably at about room temperature.

Another method for incorporating the borane into the resin is by directly treating the amine or phosphine functionality with diborane gas either in a column or batch process or with a solution of diborane in an appropriate solvent such as diethyl ether, tetrahydrofuran, and the like at temperatures from about 0° to about 150° C. preferably at about room temperature.

Those resins which contain amide functions either in the T, $R^1$, or $R^2$ groups can be converted into amines via the use of excess borohydride reagent, thereby reducing the bulk and increasing the ratio of the amount of borane to the amount of resin.

In the preparations where less than an equivalent of borohydride or diborane is utilized a mixed cationic and nonionic borane reducing agent is obtained which would remove metal complex anions and metal cations by both anionic exchange and by reduction of the metal cation or metal complex anion by the borane to the zero oxidation state.

Suitable crosslinked resins which can be utilized in the preparation of the nonionic borane reducing resins of this invention are those described in U.S. Pat. Nos. 2,675,359 granted Apr. 13, 1974; U.S. Pat. No. 3,037,052 granted May 29, 1962; U.S. Pat. No. 3,531,463 granted Sept. 29, 1970; and U.S. Pat. No. 3,663,467 granted May 16, 1972. The procedures described in these patents for making the crosslinked resins in both the gel and macroreticular form which are contained therein are all incorporated herein by reference.

The following examples are provided to illustrate the preparation of the nonionic borane reducing resins of the present invention and are not to be considered in any way as limitations on the breadth and scope thereof.

EXAMPLE I

Synthesis of the acrylic based amine-borane reducing resin

Step A. Protonation

A sample (50.0 g) of an acrylic based, macroreticular, weak base resin having a weak base capacity of 5.4 meq. of weak base per gram of dry resin is stirred with an aqueous hydrochloric acid solution containing 360 meq. of hydrochloric acid (30% excess) for 5 hours. The resin is washed with deionized water to a neutral pH, then with two 300 ml portions of acetone and then vacuum dried at 50° C. for 8 hours. Yield, 59.9 grams.

Step B. Borane Addition

To a 500 ml round bottom three neck flask equipped with a sealed mechanical stirrer, pressure compensating dropping funnel and mineral oil bubbler, is added a sample (52.8 g, 238.1 meq. of H+) of a dried acrylic based, macroreticular weak base resin (in the hydrochloride form) containing 4.51 meq. of H+ per gram of dry resin. A solution of sodium borohydride (10.0 g, 97% purity, 256 meq., 7% excess) in 250 ml of dry N,N-dimethylformamide is added rapidly with continuous stirring. The mixture is stirred at room temperature until no further hydrogen gas evolution is observed. The N,N-dimethylformamide is removed by filtration and the remaining resin is backwashed with deionized water until no chloride ion is detectable with silver nitrate and the pH is approximately seven. The resin is then vacuum dried at 30° C.

EXAMPLE II

Synthesis of the polystyrene based amine-borane reducing resin

Step A. Protonation

Utilizing the procedure in Example I, Step A, and a polystyrene based, macroreticular, weak base resin the desired intermediate protonated product is obtained.

Step B. Borane Addition

Utilizing the procedure in Example I, Step B, and a protonate polystyrene based, macroreticular, weak base resin, the desired borane addition product is obtained.

EXAMPLE III

Synthesis of polystyryl-diphenylphosphine-borane reducing resin

Step A. Preparation of polystyryl-diphenylphosphine

Utilizing the procedures in J. Org. Chem., Vol. 40, No. 11, p. 1669 (1975), the macroreticular form of the polystyryl-diphenylphosphine is prepared.

Step B. Borane Addition

A sample of macroreticular polystyryl-diphenylphosphine (10.0 g., 5.0 meq. phosphine/gram) is allowed to react with a tetrahydrofuran solution containing diborane (100 ml, 50 meq. $BH_3$). The mixture is stirred at room temperature for 3 hours. The resulting resin is washed with tetrahydrofuran and is vacuum dried.

EXAMPLE IV

Iodine Determination of Borane Concentration in Borane Reducing Resins

The presence and amount of borane functionality is determined by the reaction of the resin with an aqueous iodine solution and titration of excess iodine with a standardized solution of sodium thiosulfate. In this determination it is imperative that the amount of iodine adsorbed by the resin matrix be calculated for the blank. Thus, the amount of iodine reduced by the borane functionality is equal to the total amount of iodine removed minus the amount adsorbed by the polymer. This adsorption blank approach is only valid for borane resins containing borane concentrations approaching the theoretical amount, i.e. all weak base sites coordinated with borane.

EXAMPLE V

Reduction of Cyclohexanone to cyclohexanol with amine-borane resin in aqueous or non-aqueous media Samples of acrylic amine-borane and styrene based amine borane resins as well as their weak base analogs from which they are derived are exposed to both aqueous and tetrahydrofuran solutions of cyclohexanone of known concentration (4%) for a period of two hours. During this time no reaction of the cyclohexanone is observed as evidenced by a chromatographic determination of its original concentration. To each sample is added an amount of acid, HCl for the aqueous system and $BF_3$ for the tetrahydrofuran; in an amount equivalent to the concentration of the cyclohexanone. Both amine-borane resins revealed an immediate decrease in the concentration of cyclohexanone. The formation of cyclohexanol is observed in the aqueous system. However, no cyclohexanol is observed in the tetrahydrofuran solution which is to be expected in the presence of $BF_3$ which would complex the alcohol. The loss of cyclohexanone is however indicative of the reaction of the amine borane resin with cyclohexanone.

EXAMPLE VI

Batch equilibrium capacities for several precious metals

Batch equilibrium capacities are determined by reacting a known amount of amine-borane resin with an aqueous solution of the metal ion under investigation for a period of 16 hours with continuous shaking. The initial and final concentrations of the metal ion are determined by atomic absorption spectroscopy and capacities calculated from the difference.

Samples of amine-borane resin are reacted with aqueous solutions of $AuCl_4^-$, $PdCl_4^{-2}$, and $PtCl_6^{-2}$ of known concentration according to the above procedure.

The results are listed in the following table.

| Amine-borane resin weight in grams | Metal ion | Initial Conc. grams | Final Conc. grams | Capacity g metal/gram |
|---|---|---|---|---|
| 0.1090 | $AuCl_4^-$ | 0.315 | 0.0705 | 2.25 |
| 0.1020 | $PtCl_6^{-2}$ | 0.322 | 0.122 | 1.96 |
| 0.1020 | $PdCl_4^{-2}$ | 0.194 | 0.076 | 1.16 |

EXAMPLE VII

Precious metal recovery by combustion

Recovery of the metal from the metal filled beads is easily accomplished by burning the resin matrix away under an oxygen atmosphere.

A sample of gold filled resin (3.004 g) is combusted at 800° C. for 30 minutes in a furnace. Bright colored metalic gold beads are recovered (1.646 g) corresponding to an initial weight percent of 55%. The beads appear as uniform spheres possessing rough surfaces. Similar results are obtained from palladium and platinum filled resins under identical conditions.

EXAMPLE VIII

Catalyst formations

Samples (1.00 g) of palladium or platinum filled beads are pyrolyzed at 600° C. under a stream of nitrogen for 30 minutes. The resulting spherical beads appear as carbon spheres of high density attributed to the presence of the metal.

EXAMPLE IX

Metal reducing selectivity

The amine-borane resin reactivity for various metals is determined by placing a sample (0.10 g) in a vial and adding a concentrated solution of the metal ion or complex under investigation. The vial is allowed to stand for 3 weeks to ensure sufficient contact time. Reaction is confirmed by either a visible change in the beads such as a darkening in color, an increase in weight of the beads when washed with DI water and vacuum dried, or their inability to further reduce solutions of $AuCl_4^-$. Likewise a positive reduction of $AuCl_4^-$ indicates that no reaction with the metal ion under investigation has occurred. The following table represents those metals investigated and their ability to be reduced.

| Metal Ion | Source | Not Reduced | Reduced |
|---|---|---|---|
| $Na^+$ | NaCl | x | — |
| $K^+$ | KCl | x | — |
| $Li^+$ | LiCl | x | — |
| $Mg^{+2}$ | $MgCl_2$ | x | — |
| $Ca^{+2}$ | $CaCl_2$ | x | — |
| $Cr^{+3}$ | $CrCl_3$ | x | — |
| $Cr^{+6}$ | $K_2Cr_2O_6$ | x | — |
| $UO_2^+$ | $UO_2NO_3$ | x | — |
| $Bi^{+3}$ | $Bi(NO_3)_3$ | — | x |
| $As^{+3}$ | $As_2O_3$ | — | x |
| $Mn^{+2}$ | $MnCl_2$ | x | — |
| $Fe^{+2}$ | $FeCl_2$ | x | — |
| $Fe^{+3}$ | $FeCl_3$ | x | — |
| $Co^{+2}$ | $CoCl_2$ | x | — |
| $Ni^{+2}$ | $NiCl_2$ | x | — |
| $Cu^{+2}$ | $CuCl_2$ | x | — |
| $Zn^{+2}$ | $ZnCl_2$ | x | — |
| $Rh^{+3}$ | $RhCl_3$ | — | x |
| $Pd^{+2}$ | $PdCl_2$ | — | x |
| $Ag^{+1}$ | $AgNO_3$ | — | x |
| $Cd^{+2}$ | $CdCl_2$ | x | — |
| $Ir^{+3}$ | $IrCl_3$ | — | x |
| $Pt^{+4}$ | $H_2PtCl_6$ | — | x |
| $Au^{+3}$ | $HAuCl_4$ | — | x |
| $Hg^{+2}$ | $HgCl_2$ | — | x |
| $Sb^{+3}$ | $Sb_2O_3$ | — | x |
| $Sr^{+2}$ | $SrCl_2$ | x | — |
| $Pb^{+2}$ | $PbCl_2$ | x | — |
| $Tl^{+1}$ | $Tl_2(SO_4)$ | x | — |
| $Pb^{+4}$ | $Et_4Pb$ | x | — |
| $CH_3Hg^+$ | $CH_3HgCl^-$ | — | x |

EXAMPLE X

Analytical determination of gold

A gold solution containing 5 ppm $Au^{+3}$ (1000 ml) is allowed to react with a sample of the amine-borane resin in a column operation under very slow flows (0.5 ml/min). After loading is completed, the resin is assayed for gold and it was determined that a quantitative amount of gold is present; thus, establishing the resins utility as an analytical method for determining trace amounts of gold or other reactive trace metals.

EXAMPLE XI

Borane reducing resins differing in their polymeric backbones were synthesized by the procedures disclosed in the foregoing examples. The specific experimental procedure utilized is illustrated as follows with one particular backbone:

A sample of macroreticular dimethylaminopropylmethacrylamide (DMAPMA) resin with a total anion exchange capacity (TAEC) of 5 meq./g is converted to the hydrochloride form, rinsed with deionized water and dried in vacuo for 72 hours.

To a 500 ml round bottom flask equipped with a sealed mechanical stirrer and a vent to the hood, is added 47.6 g DMAPMA.HCl resin suspended in 200 g dimethylformamide (DMF). The stirring mixture is charged with 9.9 g sodium borohydride and is allowed to react overnight at ambient temperature. The solvent is siphoned from the beads and the resin is washed with deionized water. Yield: 54.9 g wet.

The amine borane resin is dried in vacuo at 55° for 72 hours.

Several borane reducing resins prepared by this general procedure are given in Table I below.

TABLE I

| Resin No. | Type of Resin Backbone |
|---|---|
| 1 | an acrylic resin (Amberlite ® IRA-35 resin, a product of Rohm and Haas Company) |
| 2 | a styrene resin (Amberlite ® IRA-93 resin, a product of Rohm and Haas Company) |
| 3 | A dimethylaminopropylmethacrylamide resin (DMAPMA) |

The borane reducing resins in Table I were loaded with platinum metal in the zero oxidation state by the procedures disclosed in the foregoing examples.

The following procedures are the specific procedures utilized to prepare the platinum loaded form of the borane reducing resin.

Platinum Loaded Resin A

A stock solution is prepared to contain 0.498 g $K_2PtCl_6$/100 ml deionized water. Into a 100 ml stock solution (0.20 g Pt) is added 2.000 g dried Resin No. 1 (Table I) and the resin is contacted with the solution for two days. After this period, the supernatant is siphoned from the beads and the resin is treated with about 15 ml–20 ml of stock formaldehyde solution (2.3 moles formaldehyde in 1.5-liter 1 N HCl) over 10–72 hours. The formaldehyde treatment is used to cleave any remaining N-borane group after precipitation of the metal onto the resin, thus reducing the overall yield. The sample is washed with deionized water and dried at 80°–90° C. overnight. Yield: 2.159 g dry.

Platinum Loaded Resin B

In like manner, a dried sample of Resin No. 1 weighing 7.005 g is added to 105 ml of $K_2PtCl_6$ stock solution. As specified above, the resin is first treated with the formaldehyde solution, washed, then dried. Yield: 6.774 g dry.

Platinum Loaded Resin C

In like manner, a dried sample of Resin No. 2 (TABLE I) weight 2.0012 g is added to 100 ml $K_2PtCl_6$ stock solution, then treated as specified above.

Platinum Loaded Resin D

In like manner, a dried sample of Resin No. 2 weighing 7.0013 g is added to 105 ml $K_2PtCl_6$ stock solution, then treated as above.

Platinum Loaded Resin E

In like manner, a dried sample of Resin No. 3 (TABLE I) weighing 2.0022 g is added to 100 ml $K_2PtCl_6$ solution and treated as above. Yield: 2.4196 g dry.

Pyrolyzed Platinum Loaded Resin F

A 3.00 g sample of platinum loaded resin D was pyrolyzed at 800° C. under 20% steam.

In order to test the resins A through F as hydrogenation catalysts, the following procedure was utilized with the exception that an equivalent amount of platinum resin was utilized to replace the $PtO_2$ used in this experiment.

Test Procedure 1

A standard catalytic hydrogenation with Adams' Catalyst ($PtO_2$) is conducted in a Parr hydrogenation apparatus. In a 500 ml reactor bottle is charged 0.1 g Adams' Catalyst, followed by 8.4 g cyclohexene in 200 ml absolute ethanol. The 4-liter tank, pressurized with hydrogen to 50–60 psi, is joined to the reactor bottle via a polypropylene connecting tube inserted through a stopper. The reactor bottle, sheathed with a guard screen, is stoppered, then set into the bottle holder. Air is evacuated from the reactor to a negative pressure and replaced with hydrogen gas to 40 psi. The pressure on the main tank is noted, the shaker is started and a pressure drop in the reactor is observed. When the pressure in the bottle reaches 10–15 psi, the reactor is filled with hydrogen to 40 psi. The pressure drop in the hydrogen tank is noted. This is repeated until there is no observed pressure drop in the reactor. For Adams' Catalyst, the total observed pressure drop in the hydrogen tank is 9.5 psi in 48 minutes.

Test Procedure 2

In like manner, the sample identified above as Platinum Loaded Resin A is tested for catalytic activity as described in Test Procedure 1. The total pressure drop is 9.1 psi in 71 minutes.

Test Procedure 3

In like manner, 2.58 g of the sample identified above as Platinum Loaded Resin B is tested for catalytic activity as specified in Test Procedure 1. The total pressure drop is 7.5 psi in 107 minutes.

Test Procedure 4

In like manner, the sample identified above as Platinum Loaded Resin C is tested for catalytic activity as described above. The total drop is 10.2 psi in 40 minutes.

Test Procedure 5

In like manner, the sample identified above as Platinum Loaded Resin E is tested for catalytic activity. The observed pressure drop is 10.5 psi in 117 minutes.

Test Procedure 6

The pyrolyzed resin, Resin F, is tested for catalytic activity in the manner described above. The pressure drop is 9.1 psi in 53 minutes.

Table II below summarizes the results of the above tests.

TABLE II

| Resin ID & % Pt* | Hydrogenation of Cyclohexene $H_2$ Pressure Drop (psig) | (0.1 mole) Time (min) |
|---|---|---|
| Adams' Catalyst ($PtO_2$) | 9.5 | 48 |
| Resin A (10% Pt) | 9.1 | 71 |
| Resin B (3% Pt) | 7.5 | 107 |
| Resin C (10% Pt) | 10.2 | 40 |
| Resin E (10% Pt) | 10.5 | 117 |
| Resin F (3% Pt)** | 9.1 | 53 |

*Percentage by weight Pt based on weight of resin substrate.
**Resin F is pyrolyzed version of Resin D (omitted from test).

To illustrate the suitability of various other aliphatic and aromatic copolymer backbones for preparing the amine or phosphine borane adducts to the present invention, the following experiments are conducted:

EXAMPLE XII

A sulfonamide amine weak base macroreticular resin is prepared in accordance with the teachings of U.S. Pat. No. 4,217,421.

The resin backbone copolymer is prepared by aqueous suspension polymerization of a monomer mixture of 97 parts styrene, 3 parts divinylbenzene (commercial grade=55% DVB, remainder≃EVB). The copolymer is isolated, chlorosulfonated and amidated with 1,1,9,9-tetramethyliminobispropylamine to yield a weak base anion exchange resin. This resin is then converted to the HCl form (column treated with 4% HCl and rinsed with DI water) and dried in vacuo for 72 hours.

The dry resin is suspended in 42 g DMF and 2.08 g $NaBH_4$ is added to the reaction mixture. After stirring overnight, DMF is siphoned from the mixture and the beads are washed three times with deionized water (1 hour each wash), then Buchner dried and bottled.

The sulfonamide amine borane resin thus prepared is tested for reducing power by adding 0.1 g of resin to 50 ml of a 1,000 ppm $Au^{+3}$ ($AuCl_3$) solution. If the resin is active to reduce the gold ion, the resin darkens within 10 minutes and the yellow-gold solution becomes colorless upon standing overnight. The sulfonamide amine borane resin is highly effective in reducing gold ion by this test.

EXAMPLE XIII

A mixed macroreticular/gel resin, denominated for convenience as a "hybrid" amphoteric ion exchange resin, is prepared in accordance with the teachings of U.S. Pat. No. 3,991,017, issued Nov. 9, 1976. The resin backbone copolymers are aliphatic and aromatic, the former being acylic acid (10% divinylbenzene crosslinker), and the latter vinylbenzylamine (1% DVB). A borane adduct is formed at the weak base functional sites of the hybrid resin by the method described above in Example XII. When tested for gold ion reduction by the method of Example XII, the hybrid resin borane adduct is found to be highly effective.

EXAMPLE XIV

A macroreticular weakly basic resin is produced by known aqueous suspension techniques from a dimethylaminopropylmethacrylamide/divinylbenzene (4%) monomer mixture. This is the same resin as described above as Resin No. 3 in Example XI. After the borane adduct is formed, the resin is found to be highly effective for reducing gold ions from a solution according to the method described above in Example XII.

The foregoing examples illustrate the fact that a borane adduct according to the present invention can be formed readily at any weakly basic functional site of an ion exchange resin regardless of the backbone copolymer composition or the presence of other functional ion exchange groups, even acidic groups (see Example XIII, above). The backbone copolymer merely serves as a highly inert carrier, allowing the exchange group to be fixed to a solid having good hydraulic and mechanical characteristics suitable for use in column operations.

It is well-known in the art that ion exchange copolymers containing a variety of "carbon-fixing moieties" such as sulfonate, carboxyl, amine, halogen, oxygen, sulfonate salts, carboxylate salts and quaternary amine salts may be pyrolyzed or partially pyrolyzed in an inert atmosphere to yield a carbonaceous particle substantially free of volatile components and having a carbon/hydrogen ratio of about 1.5:1 to about 20:1 (see U.S. Pat. No. 4,040,990). As used herein, the term "pyrolyzed" or "pyrolyzing" refers to the kown prior art technique described in U.S. Pat. No. 4,040,990. The term "combusting" as used herein is intended to refer to the complete or essentially complete oxidation of the backbone copolymer, including the carbon, to leave essentially only the catalytic metal.

The non-ionic borane reducing resins of this invention can be utilized in either batch or column operations and in addition to their use as reducing agents for metals, aldehydes, ketones and olefins, can also be utilized as an analytical reagent. These resins can be used to detect microquantities of metal ions in various aqueous and non-aqueous media due to their ability to quantitatively convert the metal ions to their zero oxidation state and concentrate the metal on and/or into the resin. The amount of metal present in the resultant metal containing resin can then be determined via gravimetric, spectroscopic or other analytical method and the microquantities of metal in the original volume of aqueous or non-aqueous media so treated can then be determined.

The ability of these resins to reduce ionic mercury salts and compounds and in particular methylmercury makes them especially useful in the detoxification of mercury polluted effluents.

Another area of application of the non-ionic borane reducing resins of the present invention is their use in the sugar refining industry as a decolorizing agent. In similar fashion, these resins can be utilized as reducing agents for the removal of oxide impurities in chemicals such as alcohols, glycols, amines, amides and the like.

These reducing resins can also be utilized for reducing peroxides in peroxide forming organic compounds especially in ethers such as diethylether, tetrahydrofuran, diisopropyl ether and the like. These resins can be utilized in the removal of peroxides in ethers already communicated with peroxides as well as being utilized as peroxide inhibitors in the storage or use of peroxide forming compounds.

The resins of this invention when impregnated with metals such as silver, copper, mercury, etc. can be employed in industrial applications as microbiocides in the textiles, paint, paper and laundry industries. These same resins can also find application in the removal of trace amounts of hydrogen sulfide, sulfur dioxide and the like from natural gas streams, coal gasification streams, coal and oil burning utility plants, sulfuric acid plants and the like. In these latter applications the potential high surface area of the finely divided, supported metal provides a high capacity material. The non-ionic borane reducing resins can also be utilized in elemental halogen and alkyl halide removal from aqueous and non-aqueous media via reduction to halide ion and an alkane respectively.

Certain of the non-ionic amine-borane reducing resins of this invention have applicability in organic synthesis procedures since the borane-resin adduct provides the desirable features that the reducing support is easily removed from the reaction mixture, the reduced material is attached to the resin system providing for complete separation of the product from the starting material. The reduced material can then be recovered from the resin by acid or base hydrolysis providing a pure product. The reducing support can then be chemically regenerated to the starting non-ionic amine borane reducing resin by procedures outlined above.

Another advantage of the borane reducing resins of this invention is their ability to provide a source of borane without the hazards associated with the use of this reagent. Another application for the amine-borane resins of the present invention is their use in the petroleum industry. Petroleum refining plants utilize noble metals as catalysts. These metals are presently recovered by dissolving them in aqua regia and then chemically reducing the metal chloride salts. However, the effluent from this process still contains about 10 to 15 ppm of metal ion. Anion exchange resins are presently used to remove these final trace amounts of metal. However, rhodium salts are not efficiently removed by anion exchange resins. Thus, the use of the high capacity amine-borane resins of the present invention can be used in place of the anion exchange resins in the above recovery process. The nonionic crosslinked resins containing amine or phosphine borane adducts can be advantageously employed in numerous applications as disclosed above. Other applications of these adducts which readily suggest themselves to those skilled in the art are meant to be included within the scope of the present specification and claims.

In the reduction reactions disclosed herein the borane group is oxidized forming boric acid when the oxidation/reduction is conducted in aqueous media. Because the borane group has the potential for losing six electrons in an aqueous media, it is capable of reducing six monovalent metal ions, accounting for the high capacity of the resins of the invention. In nonaqueous media, such as an organic media or a gas, the mechanism for reduction involves hydride transfer, as mentioned above, and the borane compound found may or may not be soluble in the media. In any event, hydride transfer involves loss of only three hydride ions by the borane group.

I claim:

1. A nonionic borane reducing resin which comprises a solid, crosslinked copolymer containing a plurality of amine of phosphine borane adducts of the formula:

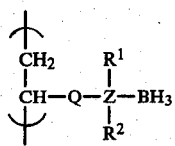

wherein

Q is a group of the formula

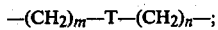

m and n are independently integers from 0 to 3;

T is the group

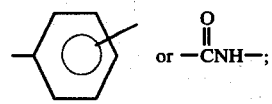

$R^1$ and $R^2$ are independently
(a) hydrogen,
(b) ($C_1$–$C_8$) optionally substituted alkyl,
(c) ($C_6$–$C_{12}$) optionally substituted aryl, and
(d) ($C_7$–$C_{12}$) optionally substituted aralkyl; and Z is nitrogen or phosphorous.

2. A resin according to claim 1 wherein $R^1$ and $R^2$ are independently hydrogen, ($C_1$–$C_8$) unsubstituted alkyl, ($C_6$–$C_{12}$) unsubstituted aryl or ($C_7$–$C_{12}$) unsubstituted aralkyl.

3. A resin according to claim 2 wherein T is the group

and Z is nitrogen.

4. A resin according to claim 1 wherein Q is

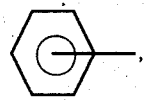

Z is nitrogen and $R^1$ and $R^2$ are independently hydrogen, ($C_1$–$C_8$) unsubstituted alkyl, ($C_6$–$C_{12}$) unsubstituted aryl or ($C_7$–$C_{12}$) unsubstituted aralkyl.

* * * * *

UNITED STATES PATENT AND TRADEMARK OFFICE
CERTIFICATE OF CORRECTION

PATENT NO. : 4,355,140

DATED : October 19, 1982

INVENTOR(S) : Larry Manziek

It is certified that error appears in the above-identified patent and that said Letters Patent is hereby corrected as shown below:

Claim 1, column 13, line 21, "of" should read -- or --.

Claim 1, column 14, line 13, "phosphorous" should read -- phosphorus --.

Signed and Sealed this

Twenty-sixth Day of July 1983.

[SEAL]

Attest:

GERALD J. MOSSINGHOFF

Attesting Officer    Commissioner of Patents and Trademarks